US006153187A

United States Patent [19]
Yacoby-Zeevi

[11] Patent Number: 6,153,187
[45] Date of Patent: Nov. 28, 2000

[54] USE OF GLYCOSAMINOGLYCANS DEGRADING ENZYMES FOR MANAGEMENT OF AIRWAY ASSOCIATED DISEASES

[75] Inventor: Oron Yacoby-Zeevi, Meitar, Israel

[73] Assignee: Insight Strategy & Marketing Ltd., Rohouot, Israel

[21] Appl. No.: 09/046,475

[22] Filed: Mar. 25, 1998

Related U.S. Application Data

[63] Continuation-in-part of application No. 08/922,170, Sep. 2, 1997, Pat. No. 5,968,822.
[51] Int. Cl.[7] .............................. A61K 38/51; C12N 9/88
[52] U.S. Cl. ................. 424/94.5; 424/94.61; 424/94.62; 424/94.6; 435/232
[58] Field of Search ............................... 424/94.5, 94.61, 424/94.62, 94.6; 435/232

[56] References Cited

U.S. PATENT DOCUMENTS

| 5,474,983 | 12/1995 | Kuna et al. | 514/12 |
|---|---|---|---|
| 5,580,862 | 12/1996 | Rosen et al. | 514/61 |

FOREIGN PATENT DOCUMENTS

| 97/11684 | 4/1997 | WIPO . |
|---|---|---|

OTHER PUBLICATIONS

Allen, E.D., "Opportunities for the Use Aerosolized $\alpha_1$—Antitrypsin for the Treatment of Cystic Fibrosis", *Chest*, 110:256S–260S, 1996.
Konstan et al, "Current Understanding of the Inflammatory Process in Cystic Fibrosis",*Pediatric Pulmonology*, 24:137–142, 1997.
Dasgupta et al, "Reduction in Viscoelasticity in Cystic Fibrosis Sputum In Vitro Using Combined Treatment with Nacystelyn and rhDNase", *Pediatric Pulmonology*, 22:161–166, 1996.
Crystal, R.G., Gene Therapy Strategies for Pulmonary Disease, *Am. J. Medicine*, 92(supp 64): 6A–44S–6A–52S (Jun. 1992).
Lieberman, J., The Appropriate Use of Mucolytic Agents, *Am. J. Medicine*, 49(1):1–4, 1970.
Boat et al, "Biochemistry of Airway Mucus Secretions", *Fed Proc*, 39:13: 3067–3074, 1980 (Abstract).
Mohapatra et al, "Alteration of Sulfation of Glycoconjugates, but not Sulftate Transport and Intracellular Inorganic Sulfate Content in Cystic Fibrosis Airway Epithelial Cells", *Pediatr Res*, 38(1): 42–48, 1995 (Abstract).
Cheng P.W. et al. "Increased Sulfation of Glycoconjugates ny Cultured Nasal Epithelial Cells from Patients with Cystic Fibrosis", *J. Clin Invest.*, 84(1):68–72, 1989 (Abstract).
Boat et al, "Epithelial Cell Dysfunction in Cystic Fibrosis: Implications for Airways Disease", *Acta Paediatr Scand Suppl*, 363:25–29, 1989.
Welch et al, "Complex Saccharide etabolism in Cystic Fibrosis Fibroblasts", Pediat Res, 9:698–702, 1975.

Schwatz et al "CpG Motifs in Bacterial DNA Cause Inflamation in the Lower Respiratory Tract", *J. Clin. Invest.*, 100(1): 68–73, 1997 (Abstract).
Hill et al, "Organ–Specific Over–Sulfation of Glycosaminoglycans and Altered Extracelluar Matrix in a Mouse Model of Cystic Fibrosis",*Biochem Mol Med*, 62(1): 113–122, 1997 (Abstract).
"Harper's Biochemistry", 24th Ed. pp. 660–685.
Chase et al, "Respiratory Mucous Secretions in Patients with Cystic Fibrosis: Relationship Between Levels of Highly Sulfated Mucin Component and Severity of the Disease", *Clinica Chimica Acta*, 132: 143–155, 1983.
Schwab et al, "Increased Adherence of *Staphylococcus Aures* From Cystic Fibrosis Lungs to Airway Epithelial Cells", *Am Rev Respir*, 148(2): 365–369, 1993 (Abstract).
Barghouthi et al, "Nonopsonic Phagocytosis of *Pseudomonas Aeruginosa* Requires Facilitated Transport of D–Glucose by Macrophages", *J. Immunol.*, 154(7): 3420–3428, 1995 (Abstract).
Moser et al, "Chronic *Pseudomonas Aeruginosa* Lung Infection is more Severe in Th2 Responding BALB/c Mice compared to Th1 Responding C3H/HeN Mice", *APMIS*, 105(11): 838–842, 1997 (Abstract).
Cowley et al, "Mucociliary Clearance in Cystic Fibrosis Knockout Mice Infected with *Pseudomonas Aeruginosa*", *Eur Respir*, 10(10): 2312–2318, 1997 (Abstract).
Zahm et al, "Early Alterations in Airway Mucociliary Clearance and Inflamation of the *Lamina Propria* in CF Mice", *Am J Physiol*, 272(3 Pt 1): C853–C859, 1997 (Abstract).
Pier et al, "Cysytic Fibrosis Transmembrane Conductance Regulator is an Epithelial Cell Receptor for Clearance of *Pseudomonas Aeruginosa* From the Lung", *Proc Natl Acad Sci USA*, 94(22): 12088–12093, 1997.
Selvan et al, "Heparan Sulfate in Immune Responses", *An. NY Acad. Sci.*, 797: 127–139, 1996.
Vlodavsky et al, "Expression of Heparanase by Platelets and Circukating Cells of the Immune System: Possible Involvement in Diapedesis and Extravasation", *Invasion Metastasis*, 12:112–127, 1992.
Nakajima et al, "Heparanases and Tumor Metastasis", *J. Cell Biochem.*, 36(2): 157–167, 1988.
Thompson et al, "Identification of Chondroitin Sulfate E in Human Lung Mast Cells",*J. Immunol.*, 140(8): 2708–2713, 1988 (Abstarct).

(List continued on next page.)

*Primary Examiner*—Rebecca E. Prouty

[57] ABSTRACT

A method of managing a patient having an accumulation of mucoid, mucopurulent or purulent material containing glycosaminoglycans, the method comprising the step of administering at least one glycosaminoglycans degrading enzyme to the patient in an amount therapeutically effective to reduce at least one of the following: the visco-elasticity of the material, pathogens infectivity and inflammation. An article of manufacture comprising an inhaler including, as an active ingredient, at least one glycosaminoglycans degrading enzyme for generating aerosols including the enzyme for management a patient having an accumulation of mucoid, mucopurulent or purulent material containing glycosaminoglycans.

13 Claims, 2 Drawing Sheets

OTHER PUBLICATIONS

Giuffre et al, "Monocyte Adhesion to Activated Aortic Endothelium: Role of L–Selectin and Heparan Sulfate Proteoglycans", *J Cell Biol,* 136(4): 945–956, 1997 (Abstarct).

Shimada et al, "Involvement of Cell Surface Heparin Sulftae in the Binding of Lipoprotein Lipase to Cultured Bovine Endothelial Cells", *J Clinical Invest,* 68(4): 995–1002, 1981 (Abstarct).

Rahmoune et al, "Chondroitin Sulfate in Sputum from Patients with Cystic Fibrosis and Chronic Bronchitis", *Am J Resp Cell & Mol Biol,* 5(4): 315–320, 1991.

Hayward et al, "Heparinase III Exerts Endothelial and Cardioprotective Effects in Feline Myocardial Ischemia–Reperfusion Injury", *J. Phar Exp Ther,* 283(3): 1032–1038, 1997 (Abstarct).

Yamaguchi et al, "Neutrophil Elastase Inhibitor Reduces Neutrophil Chemoattactant Production After Ischemia–Reperfusion in Rat Liver", *Gastroenterology,* 112(2): 551–560, 1997 (Abstract).

Matgolies et al, "Identification of a Major Heparin–Precitable Protein in Human Serum and its Relationship to Cystic Fibrosis", *Pediatr Res,* 16(3): 181–186, 1982 (Abstract).

Leong et al, "Diffrent Classes of Proteoglycans Contriute to the Attachment of *Borrelia Burgdorferi* to Cultured Endiothelial and Brain Cells", *Infect Immun,* 66(3): 994–999, 1998 (Abstract).

Asagoe et al, "Effect of Heparin on Infedtion of Cells by Equine Arteritis Virus", *J Vet Med Sci,* 59(8): 727–728, 1997 (Abstract).

Krusat et al, "Heparin–Dependent Attachment of Respiratory Syncytial Virus (RSV) to Host Cells", *Arch Virol,* 142(6): 1247–1254, 1997 (Abstract).

Alvarez–Dominguez et al, "Host Cell Heparian Sulfate Proteoglycans Mediate Attachment and Entry of *Listeria Monocytogenes,* and the Listerial Surface Protein ActA is Involved in Heparan Sulfate Receptor Recognition", *Infection & Immum,* 65(1): 78–88, 1997, (aBSTRACT).

Hagiwara et al, "Inhibitory Effect of Heparin on Red Blood Cell Invasion by *Theileria Sergenti* Merozoites", *Int J Parasitol,* 27(5): 535–539 (Abstract) 1997.

Shakibaei et al, "Dual Interaction of the Malaria Circumsporozoite Protein with the Low Density Lipoprotein Receptor–Related Protein (LRP) and Heparan Sulfate Proteoglycans", *J Exp Med,* 184(5): 1699–1711, 1996 (Abstract).

Inaba et al, "Effect of Heparinon Infection of Cells by Porcine Reproductive and Respiratory Syndrome Virus", *Am J Vet Res,* 58(5):488–491, 1997 (Abstract).

Chen et al, "Dengue Virus Infectivity Depends on Envelope Protein Bin to Target Cell Heparan Sulfate", *Nature Medicine,* 3(8): 866–871, 1997.

Gantt et al, "Cell Adhesion to a Motif Shared by the Malaria Circumsporozoite Protein and Thrombospondin is Mediated by its Glycosminoglycan–Binding Region and not by CSVTCG", *J Biol Chem,* 272(31): 19205–19213, 1997 (Abstract).

Robert et al, "Chondroitin–4–Sulphaate (Proeoglycan), a receptor for Plasmodium Falciparum–Infected Erthrocyte Adherence on Brain Microvascular Endothelial Cells", Res Immunol, 146(6): 383–93, 1995. (Abstract).

Herrera et al, "Mediation of *Trypanosoma Cruzi* Invasion by Heparan Sulfate Receptors on Host Cells and Penetrin Counter–Receptors on the Trypanosomes", *Mol & Biochem Parasit,* 65: 73–83, 1994.

USE OF GLYCOSAMINOGLYCANS DEGRADING ENZYMES FOR MANAGEMENT OF AIRWAY ASSOCIATED DISEASES

This is a continuation-in-part of U.S. patent application Ser. No. 08/922,170, filed Sep. 2, 1997 now U.S. Pat. No. 5,968,822.

FIELD AND BACKGROUND OF THE INVENTION

The present invention relates to the management of airway associated diseases and, more particularly, to the use of glycosaminoglycans degrading enzymes for the management, treatment and relieve of symptoms of respiratory diseases. Most particularly the present invention relates to a method of managing a patient having an accumulation of mucoid, mucopurulent or purulent material containing glycosaminoglycans by glycosaminoglycans degrading enzymes. The invention further relates to an inhaler article including a glycosaminoglycans degrading enzyme for effecting the management of the airway associated diseases.

Respiratory Diseases

Respiratory diseases are characterized by obstruction of the airways caused by the accumulation of thick secretions, recurrent respiratory tract infections (RTI) and progressive deterioration of lung function. The airway secretions become permanently colonized by bacteria. Cystic fibrosis (CF), the most common lethal genetic disease affecting the white population, owes its morbidity and mortality primarily to the devastating effects of chronic inflammation and infection within the pulmonary airway. It has become increasingly recognized that the host's response to Pseudomonas sp. and *Staphylococcus aureus* infection plays a paramount role in CF lung destruction and eventual development of respiratory insufficiency. A massive pulmonary influx of neutrophils, and accompanying excessive levels of neutrophil elastase (NE), can be detected in the bronchoalveolar fluid of even very young children with CF. The excess of NE adversely affects the CF airways by enhancing mucus secretion, directly injuring airway tissues, exacerbating the inflammatory process by attracting more neutrophils, and derailing opsonization and elimination of bacterial pathogens, particularly *Pseudomonas aeruginosa*. Allen ED; CHEST 1996; 110:256S–260S.

Although airway obstruction and chronic endobronchial infection have long been recognized as major factors in the pathogenesis of lung disease in CF, only recently has it been recognized that the inflammatory process itself may be responsible in a major way for destroying the lungs. The most characteristic feature of inflammation in the CF lung is the persistent infiltration of massive numbers of neutrophils into the airways. Recent bronchoalveolar lavage studies suggest that neutrophil-rich inflammation begins very early, even in infants without clinically apparent lung disease. Surprisingly, some infants have inflammation even in the apparent absence of infection, leading to the speculation that inflammation may precede infection. A number of chemoattractants from epithelial cells, macrophages, neutrophils themselves, and bacterial products contribute to the neutrophil influx. For these reasons, anti-inflammatory therapy should be initiated in early life. Additional studies are necessary to define the optimal anti-inflammatory drugs and regimens, and to confirm their long-term safety and efficacy. Konstan M W and Berger M; Pediatric Pulmonology; 1997; 24:137–42.

Routine management of CF includes a comprehensive, program that aims at maintaining normal nutrition and delaying the progression of lung disease. Regular secretion clearance, frequent antibiotics, and bronchodilators are commonly used. However, despite this early, aggressive and comprehensive management, airway inflammation and infection progress.

Several other recent approaches are in use, such as the use of glucocorticosteroids and ibuprofen to decrease inflammation, as well as recombinant human DNase (DORNASE ALFA, by Genentec Inc. USA), administered as aerosol, thinning the secretions by degrading nucleic acid polymers therein and thereby enhancing expectoration through ciliary and/or cough mechanisms, to improve pulmonary function. Other potential treatments include amiloride/uridine triphosphate and hypertonic saline aerosols. Early treatment offers the promise of reducing morbidity as well as delaying the progression of later disease. Weller P H; Pediatric Pulmonology 1997; 24:143–46.

Acetylcysteine's mucolytic action is based on the combined mucolytic activity of two different mechanisms. It reduces disulfide (S—S) bonds within the mucous gel to sulfhydryl groups (—SH), reducing the viscosity of the mucus and enhancing expectoration through ciliary and/or cough mechanisms. Dasgupta B and King M; Ped. Pulm. 1996; 22:161–6. However, it was found to be non-efficient for use in vivo since it irritates the airway mucosa and is not effective in the routes of administration used.

Secretory leukoprotease inhibitor (SLPI) is the major antiprotease of the epithelium of the upper respiratory tract providing protection against NE. The recombinant SLPI may provide a unique opportunity for protecting the lung from the damage caused by inflammatory processes not only by inducing an increase of the anti-NE protective screen, but also by improving the antioxidant protection by raising glutathione levels in the lungs, by a single drug. Neutralization of excess NE by delivering supplemental $\alpha$1-antitrypsin to the airways via aerosolization represents an exciting new potential treatment for CF lung disease.

Heart-lung or double-lung transplantation may be considered for selected patients in end stage disease; however, this strategy is severely limited by the shortage of donor organs and complications such as obliterative bronchiolitis.

Gene therapy has also been proposed as a treatment strategy and perhaps a cure for the respiratory pathophysiology of CF, but clinical trials in infants were not imminent. Three vector systems have been evaluated for their possible utility in transferring genes in a fashion that would either alter the milieu of the lung or directly alter the genetic program of lung parenchymal cells.

Two general strategies can be used: ex vivo modification of autologous cells with subsequent transplantation to the patient and in vivo modification with an appropriate vector containing the exogenous gene. Studies carried out in experimental animals show that it is theoretically possible to treat both $\alpha$1-antitrypsin deficiency and cystic fibrosis with gene therapy if the safety hurdles can be overcome to minimize the risks involved. Crystal R G; The American J. of Medicine 1992; Vol. 92 (Suppl. 6A).

The appropriate use of mucolytic agents requires some knowledge of the composition and nature of bronchial secretions. Simple, non-infected sputum is composed almost entirely of mucopolysaccharide fibers, but when infection occurs the fibers begin to fragment and to be replaced by fibers of DNA. A number of proteolytic enzymes are effective in vitro for liquefying either mucoid or purulent respiratory secretions, and both trypsin and chymotrypsin have been advocated clinically for this purpose. The observation of metaplasia in the bronchial mucosa led some to fear that trypsin aerosols may be carcinogenic, and their use declined considerably. Lieberman J; The Am. J. Med. 1970; 49(1):1–4.

Polymerization and aggregation of mucus glycoproteins create the sputum matrix. Boat T F and Cheng P W; Fed. Proc. Nov. 1980; 39(13):3067–74.

The secreted and cell surface high molecular weight glycoconjugates (HMG) generated by primary cultures of airway epithelial cells from cystic fibrosis patients are oversulfated. It may be due to perturbation in intracellular sulfate activation or transfer of activated sulfate. Mohapatra N K et al; Pediatr. Res. 1995; 38(1):42–8, Cheng et al; J. Clin. Invest. 1989; 84(1):68–72, Boat T F and Cheng P W; Acta. Ped. Scand. Suppl. 1989; 363: 25–9.

There are several reports of secretory and other abnormalities present in cultured fibroblasts from patients with cystic fibrosis. These cells have been reported to stain metachromatically with toluidine blue and to contain more glycosaminoglycans than fibroblasts from normal individuals. They have also been reported to have an abnormally high rate of glycosaminoglycan synthesis with increased release of these compounds into the medium.

The main glycosaminglycans produced by skin fibroblasts during in vitro culture were hyaluronic acid, heparan sulfates and dermatan sulfate-like materials. Welch D W and Roberts R M; Pediat. Res. 1975; 9:698–702.

The cystic fibrosis transmembrane conductance regulator (CFTR) protein which is found in the apical membrane of airway, epithelial cells, is believed to participate it the movement of sodium and chloride ions across cell membranes. Dysfunction of the CFTR is thought to lead to the loss of luminal sodium and chloride ions and water from the epithelial cells of the airway, which in turn leads to the production of a dehydrated and viscous mucus. There is in vivo evidence for an influence of CFTR on glycoconjugate sulfation and possibly other secondary manifestations of CFTR dysfunction associated with abnormalities of the extracellular matrix. Hill W G et al.; Biochem Mol. Med. 1997; 62(1):113–22.

In addition, intracellular dysfunction of the CFTR has been proposed to alter endosomal acidification. Zhang Y et al; J. Clin. Invest. 1995; 96(6):2997–3004.

A correlation was found between levels of highly sulfated carbohydrate content in mucous secretions from CF patients and the severity of their disease. Chace K V et al.; Clinica Chimica Acta. 1983; 132:143–55.

Oversulfation of a spectrum of HMG may play an important pathophysiological role by altering the properties of mucous secretions and/or the interactions between selected bacteria and HMG at the airways' surface. The high prevalence of adherent S. aureus is due either to selection of adherent strains by CF airways or to induction of an adherent phenotype by factors residing at the CF airways surface. Schwab U E et al.; Am. Rev. Respir. Dis. 1993; 148(2):365–69.

Despite a complex sputum bacteriology, the progressive decline in pulmonary function that is the hallmark of the disease is attributable to a single infecting pathogen, mucoid Pseudomonas aeruginosa. P. aeruginosa is the predominant respiratory tract pathogen in patients with CF, and its resistance to phagocytosis may contribute to its virulence. The unique glucose dependency for phagocytosis of P. aeruginosa by macrophages, and the fact that glucose is present in only negligible quantities in the endobronchial space, may contribute to the pathogenicity of this bacterial species in CF patients. Barghouthi S et al.; J. Immunol. 1995; 154(7):3420–8.

The chronic P. aeruginosa lung infection in CF is characterized by a pronounced antibody response and microcolonies surround by numerous polymorphonuclear neutrophils (PMN). Poor prognosis is correlated with a high antibody response to P. aeruginosa antigens. Following P. aeruginosa infection, mice mortality was significantly lower in C3H/HeN (Th1 responder) strain compared to BALIB/c (Th2 responder). Moser C et al.; APMIS 1997; 105(11):838–42. Additionally, observed differences in particle transport suggest that CFTR knockout mice demonstrate different mucociliary responses to infection. Cowley E A et al.; Eur. Respir. J. 1997; 10(10):2312–18.

Decreased airway mucociliary clearance and airway submucosal inflammation represent early alteration, before any airway infection. Zahm J M et al.; Am. J. Physiol. 1997 Mar; 272(3 Pt 1):C853–59.

Other findings suggest that bacterial DNA, and unmethylated CpG motifs in particular, may play an important pathogenic role in inflammatory lung disease. Schwartz D A et al.; J. Clin. Inves. 1997; 100(10):68–73.

Others suggest that CFTR clears P. aeruginosa from the lung, indicating a direct connection between mutations in CFTR and the clinical consequences of CF. Pier G B et al.; Proc. Natl. Acad. Sci. USA. 1997; 94(22):12088–93.

Prevention of the onset of the chronic infection or prevention of the dominance of the inflammation by PMNs would be important goals for treatment in CF patients.

Proteoglycans (PGs)

Proteoglycans (previously named mucopolysaccharides) are remarkably complex molecules and are found in every tissue of the body. They are associated with each other and also with other major structural components, such as collagen and elastin. Some PGs interact with certain adhesive proteins, such as fibronectin and laminin.

Glycosaminoglycans (GAGs) proteoglycans are polyanions and hence bind polycations and cations, such as $Na^+$ and $K^+$. This latter ability attracts water by osmotic pressure into the extracellular matrix and contributes to its turgor. GAGs also gel at relatively low concentrations. The long extended nature of the polysaccharide chains of GAGs and their ability to gel, allow relatively free diffusion of small molecules, but restrict the passage of large macromolecules. Because of their extended structures and the huge macromolecular aggregates they often form, they occupy a large volume of the extracellular matrix relative to proteins. Murry R K and Keeley F W; Harper's Biochemistry, 24th Ed. Ch. 57. pp. 667–85.

Heparan sulfate (HS) proteoglycans are acidic polysaccharide-protein conjugates associated with cell membranes and extracellular matrices. They bind avidly to a variety of biologic effector molecules, including extracellular matrix components, growth factor, growth factor binding proteins, cytokines, cell adhesion molecules, proteins of lipid metabolism, degradative enzymes, and protease inhibitors. Owing to these interactions, heparan sulfate proteoglycans play a dynamic role in biology, in fact most functions of the proteoglycans are attributable to the heparan sulfate chains, contributing to cell-cell interactions and cell growth and differentiation in a number of systems. It maintains tissue integrity and endothelial cell function. It serves as an adhesion molecule and presents adhesion-inducing cytokines (especially chemokines), facilitating localization and activation of leukocytes. The adhesive effect of heparan sulfate-bound chemokines can be abrogated by exposing the extracellular matrices to heparanase before or after the addition of chemokines. Fleparan sulfate modulates the activation and the action of enzymes secreted by inflammatory cells. The function of heparan sulfate changes during the course of the immune response are due to changes in the metabolism of heparan sulfate and to the differential expression of and competition between heparan sulfate-binding molecules. Selvan R S et al.; Ann. NY Acad. Sci. 1996; 797:127–139.

Other PGs and GAGs, such as hyaluronic acid, chondroitin sulfates, keratan sulfates I, II, dermatan sulfate and heparin have also important physiological functions.

GAG Degrading Enzymes

Degradation of GAGs is carried out by a battery of lysosomal hydrolases. These include certain endoglycosidases, such as, but not limited to, mammal heparanase (U.S. patent application Ser. No. 08/922,170 for recombinant and WO91/02977 for native human heparanase) and connective tissue activating peptide III (CTAP, WO95/04158 for native and U.S. Pat. No. 4,897,348 for recombinant CTAP) which degrade heparan sulfate and to a lesser extent heparin; heparinase I, II and III (U.S. Pat No. 5,389,539 for the native form and WO95/34635 A1, U.S. Pat. No. 5,714,376 and U.S. Pat. No. 5,681,733 for the recombinant form), e.g., from *Flavobacterium heparinum* and Bacillus sp., which cleave heparin-like molecules; heparitinase T-I, T-II, T-III and T-VI from *Bacillus circulans* (US. Pat. No. 5,405,759, JO 4278087 and JPO4-278087); β-glucoronidase; chondroitinase ABC (EC 4.2.2.4) from *Proteus vulgaris,* AC (EC 4.2.2.5) from *Arthrobacter aurescens* or *Flavobacterium heparinum,* B and C (EC 4.2.2) from *Flavobacterium heparinum* which degrade chondroitin sulfate, hyaluronidase from sheep or bovine testes which degrade hyaluronidase and chondroitin sulfate; various exoglycosidases (e.g., β-glucoronidase EC 3.2.1.3 1) from bovine liver, mollusks and various bacteria; and sulfatases (e.g., iduronate sulfatase) EC 3.1.6.1 from limpets (*Patella vulgaris*), *Aerobacter aerogens, Abalone entrails* and *Helix pomatia,* generally acting in sequence to degrade the various GAGs.

One important enzyme involved in the catabolism of certain GAGs is heparanase. It is an endo-β-glucuronidase that cleaves heparan sulfate at specific interchain sites. Interaction of T and B lymphocytes, platelets, granulocytes, macrophages and mast cells with the subendothelial extracellular matrix (ECM) is associated with degradation of heparan sulfate by heparanase activity. Connective tissue activating peptide III (CTAP), an α-chemokine, can act as a heparanase, and some heparanases act as adhesion molecules or as degradative enzymes depending on the pH of the micro environment. The enzyme is released from intracellular compartments (e.g., lysosomes or specific granules) in response to various activation signals (e.g., thrombin, calcium ionophore, immune complexes. antigens and mitogens), suggesting its regulated involvement in inflammation and cellular immunity. Vlodavsky I et al.; Invasion Metas. 1992; 12(2):112–27.

In contrast, various tumor cells appear to express and secrete heparanase in a constitutive manner in correlation with their metastatic potential. Nakajima M et al.; J. Cell. Biochem. 1988; 36(2):157–67.

Degradation of heparan sulfate by heparanase results in the release of heparin-binding growth factors, enzymes and plasma proteins that are sequestered by heparan sulfate in basement membranes, extracellular matrices and cell surfaces.

There is a large increase in mast cell numbers in fibrotic lung tissue, suggesting that mast cells may play a part in the pathogenesis of pulmonary fibrosis. Mast cell products stimulated the proliferation of fibroblasts, and effect was decreased by pretreatment with heparinase.

Heparan sulfate may mediate endothelial regulation of smooth muscle growth during development or pathologic pulmonary arterial remodeling. Thompson H L et al.; J. Immunol. 1988; 140(8):2708–13.

Heparan sulfate is a ligand for L-selectin which has a significant role in monocyte adhesion to artherial endothelium. Treatment of TNFα-activated aortic endothelium with heparinase inhibited monocyte attachment by approximately 80 %. Giuffre L et al.; J. Cell. Biol. 1997; 136(4):945–56.

The development of fibrosis-formation is indicated by an increase in hyaluronic acid. Measurement of the content of hyaluronic acid in bronchoalveolar fluid from chronic bronchitis patients could assess the prognosis of fibrosis-formation in these patients in medical practice. SU 1638624A to Chernik et al.

The removal of heparan sulfate form the cell surface by purified heparinase totally inhibited the binding of lipoprotein lipase by endothelial cells but the removal of chondroitin sulfate had no effect on this binding. Shimada K et al.; J. Clin. Invest. 1981; 68(4):995–1002.

Chondroitin sulfate was identified in 85 % infected sputum samples from patients with CF. A correlation between the presence of chondroitin sulfate proteoglycans in sputum and severe tracheobronchial infection in CF was suggested. Rahmoune H et al.; Am. J. Respir. Cell Mol. Biol. 1991; 5(4):315–320.

Heparinase III was found to preserve endothelial function and attenuate PMN adherence to the coronary vascular endothelium. Hayward R et al. J. Pharmacol. Exp. Ther. 1997; 283(3):1032–38.

Pretreatment of animals with heparin resulted in significantly smaller increases in the serum concentration of cytokine-induced neutrophil chemoattractant after reperfusion. Yamaguchi Y et al.; Gastroenterology 1997: 12(2) :551–60.

Young CF patients exhibit hypogammaglobulinemia. Heparin binding to serum proteins and their subsequent precipitation is reportedly increased in cystic fibrosis. 85–89% of heparin precipitable protein was in the IgG fraction. Margolies R et al.; Pediatr. Res. 1982; 16(3): 181–6.

Figure 2:
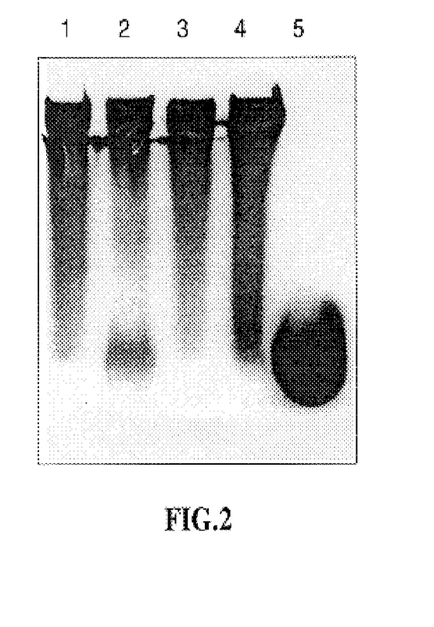

Rationale for Using GAGs Degrading Enzymes for Treatment of Respiratory Diseases The data obtained from the literature suggests a possible role for GAGs degrading enzymes, such as, but not limited to, heparanases, connective tissue activating peptide, heparinases, hyluronidases, sulfatases and chondroitinases, in reducing the viscosity of sinuses and airway secretions with associated implications on curtailing the rate of infection and inflammation. The sputum from CF patients contain at least 3% GAGs, thus contributing to its volume and viscous properties. Employing GAGs degrading enzymes can alter the visco-elasticity or the stickiness of mucous that can not be achieved by the available drugs. These enzymes, one at a time or as coctail of enzymes, may also be administered along with other pharmacologic agents used to treat the conditions listed herein, such as antibiotics, bronchodilators, anti-inflammatory agents, mucolytics (e.g. acetylcystein), and DNase. This may provide the means for a synergistic effect, lower the effective doses used for every drug by itself and reduce the frequency of drug therapy. In addition to their mucolytic properties these enzymes (especially heparanases and heparinases) may reduce the rate of infection by degrading heparan sulfate which serves as the hosts' cell ligand for attachment of many microorganisms and parasites. Heparinase I and III inhibited the binding and invasion of various bacteria (*Borrelia burgdorferi, Listeria monocytogenes*), viruses (Equine Arteritis Virus, Reproductive and Respiratory syncytial Virus, Dengue Virus, Herpes Symplex Virus) and protozoa (*Plasmodium falciparum* and *berghei, Theileria sergenti, Trypanosoma cruzi*) into host cells. Leong J M et al.; Infec. Immun. 1998; 66(3):994–9, Asagoe T et al.; J. Vet Med Sci. 1997; 59(8):727–8, Krusat T and Streckert H J; Arch. Virol. 1997; 142(6):1247–54, Alvaarez-Dominguez C et al.; Infect Immun 1997; 65(1):78–88, Shakibaei M and Frevert U; J. Exp. Med 1996; 184(5):1699–1711, Hagiwara K et al.; Int. J. Parasitol. 1997; 27(5):535–9, Jusa E R et al.; Am. J. Vet. Res. 1997; 58(5):488–91, Chen Y et al.; Nature Med. 1997; 3(8):688–71, Robert C et al.; Trd. Immunol. 1995; 146(6) :383–93, Gantt S M et al.; J. Biol Chem. 1977; 272(31) :19205–213. Furthermore, it is suggested that these enzymes may reduce inflammation by inhibiting the infiltration of inflammatory cells to the affected tissue. They can abrogate the adhesive effects of chemokines and inhibit the attachment of inflammatory cells to vascular endothelium. Reduction and/or prevention of chronic infection will reduce tissue damage, which will improve the patients quality of life and prolong their life span.

SUMMARY OF THE INVENTION

According to the present invention there is provided a method of managing airway associated disease which can be used for the management, treatment and relieve of symptoms of respiratory diseases and sinusitis. Further provided is an inhaler for effecting this method.

According to further features in preferred embodiments of the invention described below, provided is a method of managing a patient having an accumulation of mucoid, mucopurulent or purulent material containing glycosaminoglycans, the method comprising the step of administering at least one glycosaminoglycans degrading enzyme to the patient in an amount therapeutically effective to reduce at least one of the following: the visco-elasticity of the material, pathogens infectivity and inflammation. The glycosaminoglycans containing material is typically associated with an airway associated disease.

According to still further features in the described preferred embodiments the administration is via inhalation of aerosol.

Therefore, according to further features in preferred embodiments of the invention described below, provided is an article of manufacture comprising an inhaler including, as an active ingredient, at least one glycosaminoglycans degrading enzyme for generating aerosols including the enzyme for management a patient having an accumulation of mucoid, mucopurulent or purulent material containing glycosaminoglycans. Thus, the inhaler serves for generating an aerosol cloud comprising, as an active ingredient, at least one glycosaminoglycans degrading enzyme for management of the patient.

According to still further features in the described preferred embodiments the glycosaminoglycans degrading enzyme is selected from the group consisting of heparanases, connective tissue activating peptide, heparitinases, heparinases, hyluronidases, sulfatases, glucoronidases and chondroitinases.

According to still further features in the described preferred embodiments the glycosaminoglycans degrading enzyme is a native or recombinant enzyme.

According to still further features in the described preferred embodiments the glycosaminoglycans degrading enzyme is of an origin selected from the group consisting of humans, animals, fungi, algae, plants and bacteria, either native or recombinant.

According to still further features in the described preferred embodiments the patient has a disease selected from the group consisting of cystic fibrosis, α1-antitrypsin deficiency, chronic bronchitis, pulmonary emphysema, infectious pneumonia, chronic obstructive lung/pulmonary disease (COLD/COPD), asthma, tuberculosis, fungal infections, airway manifestations of mucopolysaccharidoses I, II, IIIA, IIIB, IIIC, VI and VII and sinusitis.

According to still further features in the described preferred embodiments managing the patient results in improved clearance of lung secretions and reduce the frequency of respiratory infections and inflammation requiring parenteral antibiotics and anti-inflammatory drugs.

According to still further features in the described preferred embodiments managing the patient results in improved pulmonary function.

According to still further features in the described preferred embodiments the method further comprising the step of further administering at least one conventional substance to the patient, either via coadministration or via successive administration. In the former case the inhaler preferably further includes, as an additional active ingredient(s), the conventional substance(s), for generating an aerosol cloud further comprising, as active ingredients, the conventional substance(s).

According to still further features in the described preferred embodiments the conventional substance is selected from the group consisting of DNase, antibiotics, acetylcysteine, trypsin, chymotrypsin, glucocorticosteroids, ibuprofen, amiloride triphosphate, uridine triphosphate, hypertonic saline, secretory leukoprotease inhibitors, bronchodilators, anti-inflammatory agents, mucolytics and α1-antitrypsin.

The present invention successfully addresses the shortcomings of the presently known configurations by providing a method in which a polymeric component of airway secretions which is associated with viscosity of the secretions, with inflammation and further with pathogen infection mechanisms is degraded. This is achieved according to the present invention by administration of at least one glycosaminoglycans degrading enzyme, preferably as an aerosol, to the patient.

BRIEF DESCRIPTION OF THE DRAWINGS

The invention herein described, by way of example only, with reference to the accompanying drawings, wherein:

FIG. 1 is a cross sectional view of an inhaler which includes an glycosaminoglycans degrading enzyme according to one aspect of the present invention.

FIG. 2 demonstrates the degradation of glycosaminoglycans following incubation with various substances including the glycosaminoglycans degrading enzymes heparanase and heparinase. Following 24 hours of incubation with saline (lane 3), heparanase (lane 4), DNase I (lane 2) and heparinase III (lane 1) (for detailed treatment conditions see Table 1) at 37° C., samples derived from the first patient were centrifuged and the supernatant was loaded on a 7.5% polyacrylamide native gel and electrophoresis was performed. Bromophenol blue as a size marker was loaded on lane 5.

FIG. 5 demonstrates polysaccharides degradation products in sputum of CF patient incubated with heparanase. Following 24 hours of incubation with various substances as indicated (concentrations are as listed in table 2) samples taken from the second CF patient were centrifuged for 10 minutes at 13,000 rpm and 10% of the total supernatants' volume were taken for a carbazole reaction.

FIG. 6 demonstrates the presence of glycosaminoglycans in sputum of CF patients. Sputum samples from CF patients were tested for the presence of glycosaminoglycans using the FACE glycosaminoglycans identification kit by Glyco Inc., Novato Calif. Two sputum samples from different CF patients were analyzed and the hydrolysis products are shown in lanes 1 and 2. Pure heparan sulfate and heparin (lanes 3 and 4, respectively), were used as positive controls. The hydrolysis products of heparan sulfate and heparin after degradation by heparanase are also shown (lanes 5 and 6, respectively). The monosaccharide standard ladder supplied with the kit is shown in lane 7 (100 pmol per each monosaccharide).

DESCRIPTION OF THE PREFERRED EMBODIMENTS

The present invention is of a method of managing patient having an accumulation of mucoid, mucopurulent or purulent material containing glycosaminoglycans typically associated with airway associated disease which can be used for the management, treatment and relieve of symptoms of respiratory diseases and sinusitis. Specifically, the present invention can be used for thinning, liquefying and reducing adhesivity of viscous airway secretions associated with such diseases by administration of glycosaminoglycans degrading enzyme(s) into the airways of patients. The present invention is further of an inhaler which contains glycosaminoglycans degrading enzyme(s) for effecting this method.

The principles and operation of the method and inhaler according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Thus, in accordance with the teachings of the present invention there is provided a method of managing a patient having an accumulation of mucoid, mucopurulent or purulent material containing glycosaminoglycans, typically associated with an airway associated disease, such as a respiratory disease or sinusitis, for relieving symptoms associated with secretions associated with the disease, the method comprising the step of administering to airways at least one glycosaminoglycans degrading enzyme to the patient in an amount therapeutically effective to reduce at least one of the following: the visco-elasticity of the material, pathogens infectivity and inflammation. Administration t airways is preferably effected by inhalation.

As used herein, the term "glycosaminoglycans" refers to polysaccharide-protein conjugates, such as, but not limited to, heparan sulfate, hyaluronic acid, chondroitin sulfate, keratan sulfate I, II, dermatan sulfate and heparin.

As used herein, the term "airway" refers to any part of the breathing system, including the lungs and the respiratory tract and nose.

As used herein the term "airway associated disease" refers to any disease which affects the airway of a patient to secrete abnormal amounts or composition of secretions, or that reduces the ability of the airway to eliminate secretions.

As used herein the term "patient" refers to animals having a pulmonary system, including human beings.

Figure 1:
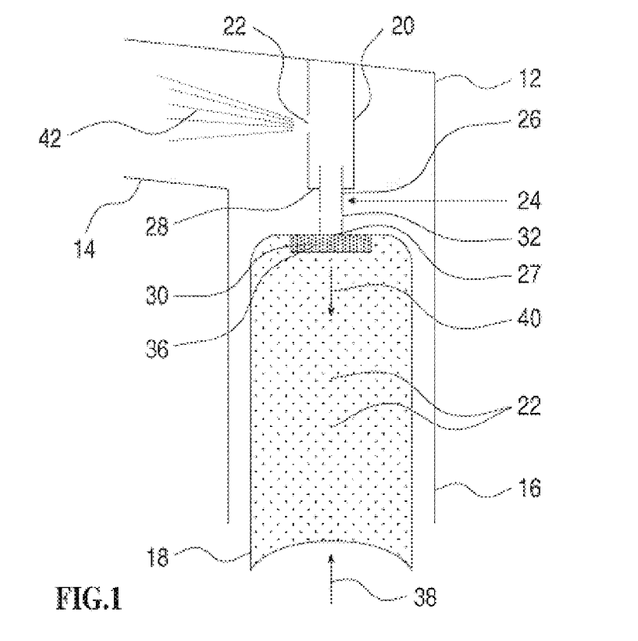

Referring now to the drawings, FIG. 1 illustrates an inhaler according to the present invention, which is referred to hereinbelow as inhaler 10.

Inhaler 10 includes a housing 12 featuring an inhaling end 14 and a container engaging end 16, adapted for engaging an aerosol generating container 18. Housing 12 is supplemented with an inner aerosol guide 20, having an aerosol outlet opening 22 positioned to direct aerosol generated by container 18 out of housing 12 via inhaling end 14.

Container 18 contains, as an active ingredient, at least one glycosaminoglycans degrading enzyme marked in FIG. 1 by dots 22. Enzyme 22 may be in a particles form (e.g., powder, slow release particles) or in suspension (e.g., aqueous suspension). In any case, container 18 is preferably pressurized.

Container 18 is equipped with an aerosol releasing valve 24 featuring a tube 26 which protrudes via an opening 27 formed in container 18 and which fits into a distal opening 28 formed in guide 20. Valve 24 further includes a sealing disc 30, connected to tube 26 and engaged within container 18. Tube 26 is formed with at least one releasing hole 32.

The operation of inhaler 10 is as follows. A user inserts container 18 into housing 12, such that tube 26 is firmly engaged by distal opening 28 of guide 20. At this stage, due to the pressure within container 18, disc 30 of valve 24 is pressed against the upper inner walls 36 of container 18, so as to seal container 18. At this stage inhaler 10 is ready for actuation.

During actuation the following events take place. Holding housing 12 with his fingers, the user, using his thumb, pushes container 18, as indicated by arrow 38, deeper into housing 12. As a result, tube 26 is pushed into container 18, so that (i) disc 30, as indicated by arrow 40, is retrieved away for walls 36; and (ii) holes 32 and therefore tube 26 become in fluid communication with container 18.

Due to the pressure within container 18, the width of tube 20, the diameter of holes 32 and other features which are well known in the art of inhalers, yet are not described herein in detail, the content of container 18 is injected via tube 22, guide 20 and end 14 as an aerosol cloud 42. Cloud 42 is of sufficient energy and active ingredients concentration, such that an effective concentration will be delivered to the airway of the patient.

Allowing container 18 to return to its relaxed position ends the process, rendering inhaler 10 ready for another actuation.

The above provides description of a very simple inhaler. More advanced inhalers which include, for example, equal dose release mechanisms and/or dose control mechanisms are well known in the art, one example are the inhalers distributed by GLAXO for the treatment of asthma.

Other inhalers are not pressurized unless actuated, whereas actuating ensures both application of pressure and release of aerosol, e.g., the microdosers by Zyma SA Nyon, Switzerland.

Yet, other inhalers used for prolonged inhalations (e.g., in the orders of minutes to hours) are also known. These inhalers are electrically operated and are used to provide air enriched with various substances to patients.

There is, thus, no intention to limit the scope of the present invention to any specific design of inhaler. As used herein, the term "inhaler", thus, refers to any article of manufacture capable of generating aerosol, to be inhaled by a user.

According to a preferred embodiment of the present invention the glycosaminoglycans degrading enzyme(s) are one or combination of heparanases, connective tissue activating peptide, glucoronidases, heparitinases, heparinases, hyluronidases, sulfatases and chondroitinases. These enzymes are capable of catalytic hydrolysis of glycosaminoglycans at various enzyme specific sites.

Any of the enzymes employed may be a native enzyme, i.e., extracted from cells or organisms producing the enzyme, either human beings, animals, fungi, algae, plants or bacteria, or in a recombinant form.

A recombinant form of, for example, human heparanase is disclosed in U.S. patent application Ser. No. 08/922,170, which is incorporated by reference as if fully set forth herein. A native form of human heparanase is disclosed in WO91/02977, which is incorporated by reference as if fully set forth herein.

The diseases to which management is offered according to the present invention include airway associated or respiratory diseases, such as, but not limited to, cystic fibrosis, α1-antitrypsin deficiency, chronic bronchitis, pulmonary emphysema, infectious pneumonia, chronic obstructive lung/pulmonary disease (COLD/COPD), asthma, tuberculosis, fungal infections, airway manifestations of mucopolysaccharidoses I, II, IIIA, IIIB, IIIC, VI and VII, or sinusitis, which affects the nasal airway.

Managing the disease according to the present invention results in improved clearance of lung secretions and reduce the frequency of respiratory infections and inflammation requiring parenteral antibiotics and anti-inflammatory drugs. It thus results in improved pulmonary function.

According to a preferred embodiment of the present invention the method further includes a step of administering at least one conventional substance to the patient. Administration may be effected by coadministartion of the conventional substance along with the glycosaminoglycans degrading enzyme(s) or successive administrations thereof. Coadministration may be effected by an inhaler including both the glycosaminoglycans degrading enzyme(s) and the conventional substance(s).

As used herein the term "conventional Substance" refers to pharmacologic agents currently used to treat patients having an accumulation of mucoid, mucopurulent or purulent material, e.g., in their airways. These include, for example, DNase, antibiotics, acetylcysteine, trypsin, chymotrypsin, glucocorticosteroids, ibuprofen, amiloride triphosphate, uridine triphosphate, hypertonic saline, secretory leukoprotease inhibitor, bronchodilators, anti-inflammatory agents, mucolytics, and/or α1-antitrypsin.

The inhaled enzyme according to the present invention is preferably administered as an aerosol, such that better access of active ingredients to the airway of the patient is achieved. The aerosol may be in a liquid aerosol (also known as spray), wherein tiny drops of liquid including the enzyme form the aerosol. Alternatively, the aerosol may be particles aerosol. In the latter case, slow release particles may be envisaged for some applications Alternatively, an immobilized enzyme to a water insoluble support, similar to that described with respect to DNase in PCT/US89/05744, which is incorporated by reference as if fully set forth herein, can be used for prolonged action. However, in severe cases intra-trachealy administration may be considered.

When the enzyme hits its target in, for example, the airway of the patient, the catalytic activity of the enzyme ensures degradation of glycosaminoglycans in secretions present in therein, thereby reducing the viscosity and adhesivity of the secretions and enhancing expectoration through ciliary and/or cough mechanisms. Furthermore, since cellular glycosaminoglycans are involved in inflammatory and pathogen infection mechanisms, their elimination reduces the susceptibility to such effects.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates.

Thus, according to the present invention glycosaminoglycans degrading enzymes, such as, but not limited to, heparanases, connective tissue activating peptide, heparinases, glucoronidases, heparitinases, hyaluronidases, sulfatases and chondroitinases are used, alone, in combination, or in combination with conventional substances, preferably as aerosol, for the management of diseases, such as, but not limited to, cystic fibrosis, α1-antitrypsin deficiency, chronic bronchitis, pulmonary emphysema, infectious pneumonia, chronic obstructive lung/pulmonary disease (COLD/COPD), asthma, tuberculosis, fungal infections and airway manifestations of MPS (mucopolysaccharidoses) I, II, IIIA, IIIB, IIIC, VI, VII, to improve clearance of lung secretions and reduce the frequency of respiratory infections and/or inflammation.

EXAMPLES

Reference is now made to the following examples, which together with the above descriptions, illustrate the invention in a non limiting fashion.

Materials and Methods

Sputum samples: Sputum samples were collected from CF patients following physiotherapy. Samples were divided into SARSTEDT 1.5 ml micro test tubes, approximately 300 mg test material per tube.

Enzymes and chemicals: Recombinant human heparanase was synthesized by insect cells transfected with baculovirus containing the encoding sequence of the human heparanase gene (U.S. patent application Ser. No. 08/922,170), Heparinase III and hyaluronidase were obtained from Sigma Chemicals, acetylcystein (Mucomystr 20% solution, Bristol-Myers Squibb Co.) Bovine pancreatic RQ1 RNase-free DNase was purchased from Promega. Heparan sulfate was obtained from Kabi-Pharmacia, Sweden. Tetraborate and carbazole were obtained from Sigma.

Pourability assay: Sputum samples with the various test materials were incubated at 37° C. for different time periods. Pourability was assessed by inverting the tubes and observing the movement of sputum on the side of the tube.

Figure 3:
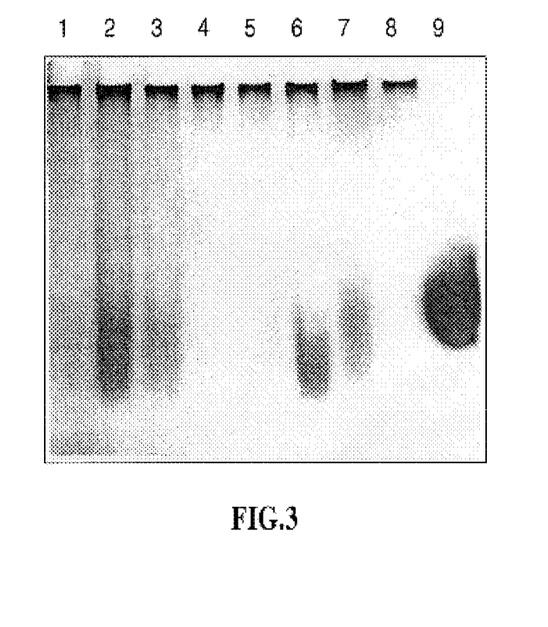
FIG. 3 demonstrates the degradation of glycosaminoglycans following incubation with various substances including the glycosaminoglycans degrading enzymes heparanase and heparinase. Following 24 hours of incubation with saline (lane 1), heparanase (lane 2), heparinase II (lane 3), DNase I (lane 4), inactivate heparanase (lane 5). heparanase+DNase I (lane 6), heparinase II+DNase I (lane 7) and inactivated DNase I (lane 8) (for detailed treatment conditions see Table 2) at 37° C., samples derived from the second patient were centrifuged and the supernatants were loaded on a 7.5% polyacrylamide native gel and electrophoresis was performed. Bromophenol blue as a size marker was loaded on lane 9.
Figure 4:
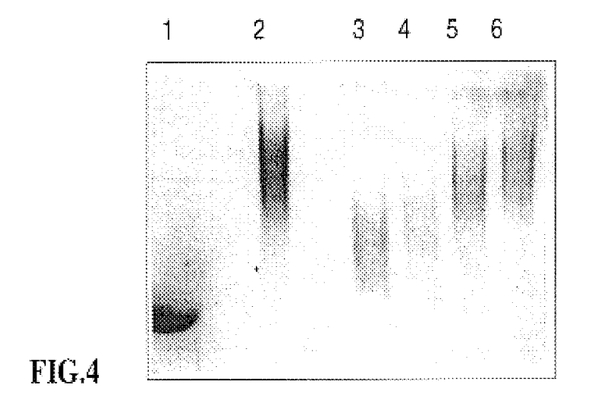
FIG. 4 demonstrates the effect of heparanase on heparan sulfate degradation as a function of incubation time. Six mg heparan sulfate were incubated with 10 µg/ml heparanase for 0 (lane 6), 1 (lane 5), 3 (lane 4) and 6 (lane 3) hours. Untreated heparan sulfate and bromophenol blue are shown in lanes 2 and 1, respectively.

Gel electrophoresis: Following 24 hours of incubation at 37° C., samples were centrifuged 10 minutes at 13,000 rpm. Supernatants were collected and loaded on a native 7.5% polyacrylamide gels. Staining of the gels was carried out by soaking in a solution containing 0.1% methylen blue and 50% ethanol for 10 minutes, followed by destaining with water (FIGS. 2–4).

Figure 5:
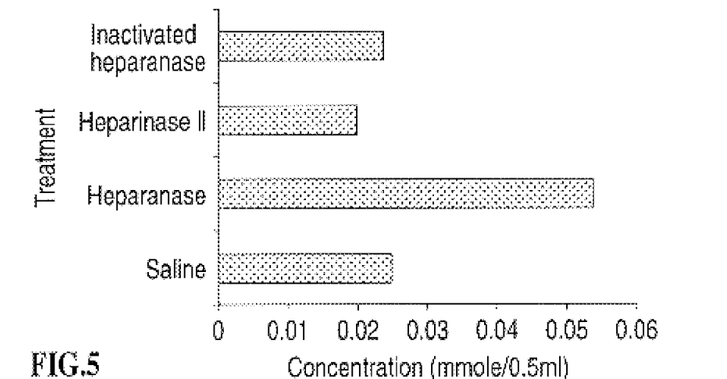

Carbazole reaction for the detection of degraded polysaccharides: Following 24 hours of incubation at 37° C., samples were centrifuged 10 minutes at 13,000 rpm. Supernatants were collected, and 10% of the total volume (20 microliters) were diluted to make a final volume of 0.5 milliliters. Sulfuric acid-tetraborate (0.5% tetraborate in 97.5% sulfuric acid), 2.5 milliliters, was added to each sample and vortexed. Samples were cooled in ice water bath and then boiled for 20 minutes, followed by cooling in water bath. Carbazole reagent 0.125%, 0.1 milliliters, was added to each sample, then the samples were vortexed, boiled for 10 minutes, and cooled in ice water bath. Then, samples were warmed to room temperature by immersing in room temperature water. Absorbance was read at 530 nanometers (FIG. 5). A standard curve was prepared by using glucuronolactone solution at various concentrations. Following the protocol by Bitter T and Muir H M; Anal. Biochem. 1962; 4:330–334.

Figure 6:
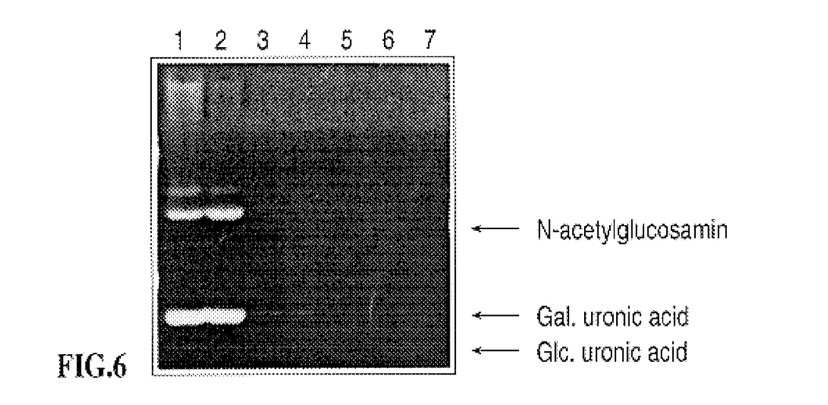

Identification of glycosaminoglycans in sputum samples from CF patients: Identification of glycosaminoglycans in sputum samples from CF patients was effected by the FACE glycosaminoglycans identification kit by Glyco Inc., Novato Calif., according to the manufacturer's instructions (FIG. 6).

Experimental Results

Heparanase reduces the viscosity of CF sputum, transforming it from a non-flowing gel to a flowing liquid. Table 1 below shows the results of a qualitative experiment in which reduction in sputum viscosity was determined by the pourability assay. Sputum samples from one CF patient were incubated at 37° C. with either saline, purified recombinant human heparanase, heparinase III, bovine DNase I, acetylcystein and heat inactivated heparanase, or with no added solution.

Sputum samples from another CF patient were incubated at 37° C. with either saline, purified recombinant human heparanase, heparinase II, bovine DNase I, acetylcystein, DNase I with heparanase, DNase I with heparinase III, heat inactivated DNase I and heat inactivated heparanase, or with no added solution the pourability was assessed following various periods of incubation times by inverting the incubation 1.5 ml microtubes and observing the movement of sputum on the side of the tube. These results are summarized in Table 2 below.

Heparanase, heparinase III, DNase I and acetylcystein, increased the pourability of CF sputum from the first patient in a time-dependent manner, whereas saline did not (Table 1).

Heparanase, heparinase II, DNase I, acetylcystein and the combination of DNase I with heparanase and to a lesser extent the combination of DNase I with heparinase II, increased the pourability of CF sputum from the second patient in a time-dependent manner, but saline and heat inactivated (10 minutes at 100° C.) heparanase or DNase I did not increase the pourability of the sputum sample (Table 2).

TABLE 1

| Treatment | Test material | Weight of sample | Viscosity 15' | 2 h | 4 h | 8 h |
|---|---|---|---|---|---|---|
| Saline | 20 µl | 314 mg | 0 | 0 | 0 | 0 |
| Heparanase | 10 µl saline + 10 µl heparanase (2 µg) | 320 mg | 0 | 1 | 2 | 3 |
| Heparinase III | 10 µl saline + 10 µl heparinase III (0.5 u) | 225 mg | 0 | 0 | 1 | 3 |
| Acetylcystein | 10 µl saline + 10 µl 20% acetylcystein | 251 mg | 3 | 3 | 3 | 3 |
| DNase I | 10 ml saline + 10 ml DNase I (10 u) | 221 mg | 0 | 1 | 3 | 3 |

TABLE 2

| Treatment | Test material | Weight of sample | Viscosity 15' | 1 h | 2 h | 4 h |
|---|---|---|---|---|---|---|
| No treatment | — | 181 mg | 0 | 0 | 1 | 0 |
| Saline | 20 µl | 186 mg | 1 | 1 | 1 | 0 |
| Heparanase | 10 µl saline + 10 µl heparanase (2 µg) | 188 mg | 1 | 2 | 2 | 2 |
| Heparinase II | 10 µl saline + 10 µl heparinase III (0.5 µ) | 189 mg | 1 | 2 | 2 | 1 |
| Acetylcystein | 10 µl saline + 10 µl 20% acetylcystein | 195 mg | 3 | 3 | 3 | 3 |
| DNase I | 10 ml saline + 10 ml DNase I (10 u) | 190 mg | 0 | 1 | 2 | 3 |
| Heat Inact. heparanase | 10 µl saline + 10 µl heparanase (2 µg) | 173 mg | 0 | 2 | 2 | 1 |
| Heat Inact. DNase I | 10 ml saline + 10 ml DNase I (10 u) | 188 mg | 0 | 1 | 1 | 0 |

TABLE 2-continued

| Treatment | Test material | Weight of sample | Viscosity | | | |
|---|---|---|---|---|---|---|
| | | | 15' | 1 h | 2 h | 4 h |
| DNase I + heparanase | 10 µl saline + 5 µl DNase I (5 u), 5 µl heparanase (1 µg) | 193 mg | 1 | 2 | 2 | 3 |
| DNase + heparinase II | 10 µl saline + 5 µl DNase I (5 u), 5 µl heparinase II (0.5 u) | 198 mg | 1 | 0 | 1 | 2 |

In Tables 1 and 2, pourability was assessed qualitatively following various periods of incubation at 37° C. by inverting the tubes and observing the movement of sputum, where 0=no movement, 1=it takes 10 sec for 50% of sample to run down the tube, 2=it takes 5 seconds for over 50% of sample to run down the tube, 3=movement of all the sputum freely down the tube (within 1 second).

The effect of acetylcystein was the most prominent one. The reduction in aminoglycans polysaccharide chains size is shown in FIGS. 2 and 3. After 24 hours of incubation at 37° C. samples were centrifuged and the supernatant was loaded on a polyacrylamide native gel. The results show that only where heparanase was present (lane 4 FIG. 2; lane 2 FIG. 3), and to a lesser extent heparinase III or II (lane 1, FIG. 2; lane 3, FIG. 3, respectively), methylen blue stainable degraded material was detected.

FIG. 4 shows the effect of heparanase on pure heparan sulfate (Kabi-Pharmacia) degradation as a function of incubation time. Please note the degradation of the substrate by the enzyme as shown in lanes 3–6 as compared with lane 2 (no enzyme added).

To test the presence of degraded polysaccharides in supernatants obtained from sputum samples of CF patients, following 24 hours of incubation at 37° C. with various substances, the carbazole reaction was performed. In this assay carbazole reagent binds to iduronic acid, a degradation product of polysaccharides, and the concentration of the reagent-acid complex is measured spectroscopically. The results are summarized in FIG. 5 and show that samples that were incubated with heparanase have significantly more iduronic acid in the supernatant as compared with controls (saline and heat inactivated heparanase).

In order to find what is the amount of GAG's in sputum samples, the FACE glycosaminoglycans identification kit by Glyco Inc., was employed. The results shown in FIG. 6 demonstrate that a 5 microliters sample contains approximately 500 pmol of each monosaccharide indicated. Furthermore, the results show that heparan sulfate is present, in relatively large amounts, in the sputum samples (lanes 1 and 2) as compared to products produced by hydrolysis of pure heparan sulfate (Kabi-Pharmacia), as shown in lane 4.

Thus, according to the present invention glycosaminoglycans degrading enzymes, such as, but not limited to, heparanases, connective tissue activating peptide, heparinases, glucoronidases, heparitinases, hyaluronidases, sulfatases and chondroitinases are used, alone, in combination, or in combination with conventional substances, preferably as aerosols, for the management of respiratory diseases such as, but not limited to, cystic fibrosis, α1-antitrypsin deficiency, chronic bronchitis, pulmonary emphysema, infectious pneumonia, chronic obstructive lung/pulmonary disease (COLD/COPD), asthma, tuberculosis, fungal infections and airway manifestations of MPS (mucopolysaccharidoses) I, II, IIIA, IIIB, IIIC, VI, VII, to improve clearance of lung secretions and reduce the frequency of respiratory infections and/or inflammation requiring parenteral antibiotics and/or anti-inflammatory drugs respectively, and to improve pulmonary function, due to their mucolytic action and anti-inflammatory properties. It is also recommended for the treatment of sinusitis to improve clearance of secretions, and reduce the use of surgical interventions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of reducing, in a patient, the visco-elasticity of mucoid, mucopurulent or purulent material containing glycosaminoglycans, the method comprising the step of administering to the patient at least one glycosaminoglycans degrading enzyme selected from the group consisting of heparanase and heparinase in an amount therapeutically effective to reduce the visco-elasticity of the material.

2. The method of claim 1, wherein said glycosaminoglycans containing material is associated with an airway disease.

3. The method of claim 1, wherein said administration is via inhalation of aerosol.

4. The method of claim 1, wherein said heparanase is a native heparanase.

5. The method of claim 1, wherein said heparanase is a recombinant heparanase.

6. The method of claim 1, wherein said heparanase is a human heparanase.

7. The method of claim 1, wherein said glycosaminoglycans degrading enzyme is native.

8. The method of claim 1, wherein said glycosaminoglycans degrading enzyme is recombinant.

9. The method of claim 1, wherein said at least one glycosaminoglycans degrading enzyme is of an origin selected from the group consisting of humans, animals, fungi, algae, plants and bacteria.

10. The method of claim 1, wherein said patient has a disease selected from the group consisting of cystic fibrosis, α1-antitrypsin deficiency, chronic bronchitis, pulmonary emphysema, infectious pneumonia, chronic obstructive lung/pulmonary disease (COLD/COPD), asthma, tuberculosis, fungal infections, airway manifestations of mucopolysaccharidoses I, II, IIIA, IIIB, IIIC, VI and VII and sinusitis.

11. The method of claim 1, wherein the patient has cystic fibrosis.

12. The method of claim 1, further comprising the step of administering at least one conventional substance to the patient.

13. The method of claim 12, wherein said conventional substance is selected from the group consisting of DNase, antibiotics, acetylcysteine, trypsin, chymotrypsin, glucocorticosteroids, ibuprofen, amiloride triphosphate, uridine triphosphate, hypertonic saline, secretory leukoprotease inhibitor, bronchodilators, anti-inflammatory agents, mucolytics and α1-antitrypsin.

* * * * *